United States Patent
Kim (10) Patent No.: US 12,343,201 B2
(45) Date of Patent: Jul. 1, 2025

(54) ENDOSCOPIC IMAGE DIAGNOSIS DEVICE HAVING DISPOSABLE ULTRASOUND PROBE

(71) Applicant: UNIVERSITY INDUSTRY FOUNDATION, YONSEI UNIVERSITY WONJU CAMPUS, Gangwon-do (KR)

(72) Inventor: Hee Man Kim, Gangwon-do (KR)

(73) Assignee: UNIVERSITY INDUSTRY FOUNDATION, YONSEI UNIVERSITY WONJU CAMPUS, Gangwon-Do (KR)

(*) Notice: Subject to any disclaimer, the term of this patent is extended or adjusted under 35 U.S.C. 154(b) by 175 days.

(21) Appl. No.: 18/005,249

(22) PCT Filed: Jul. 13, 2021

(86) PCT No.: PCT/KR2021/008928
§ 371 (c)(1),
(2) Date: Jan. 12, 2023

(87) PCT Pub. No.: WO2022/014999
PCT Pub. Date: Jan. 20, 2022

(65) Prior Publication Data
US 2023/0248332 A1 Aug. 10, 2023

(30) Foreign Application Priority Data
Jul. 13, 2020 (KR) .................. 10-2020-0086154
Jul. 13, 2020 (KR) .................. 10-2020-0086155

(51) Int. Cl.
*A61B 8/12* (2006.01)
*A61B 8/00* (2006.01)

(52) U.S. Cl.
CPC ............... *A61B 8/12* (2013.01); *A61B 8/461* (2013.01)

(58) Field of Classification Search
CPC ........... A61B 8/12; A61B 8/461; A61B 8/085; A61B 8/4494; A61B 1/00; A61B 1/05;
(Continued)

(56) References Cited

U.S. PATENT DOCUMENTS 5,471,988 A * 12/1995 Fujio ...................... A61B 8/445
601/3
6,270,460 B1 * 8/2001 McCartan ............ A61B 8/4438
600/459
(Continued)

FOREIGN PATENT DOCUMENTS

JP 4300378 B2 7/2009
WO 2018016487 A1 1/2018
(Continued)

OTHER PUBLICATIONS

International Search Report for International Application No. PCT/KR2021/008928 dated Oct. 26, 2021, 7 pages including English Translation.

*Primary Examiner* — Baisakhi Roy
*Assistant Examiner* — Kaitlyn E Sebastian
(74) *Attorney, Agent, or Firm* — MH2 Technology Law Group, LLP (57) ABSTRACT

An endoscopic image diagnosis device having a disposable ultrasound probe is disclosed. An endoscopic image diagnosis device of the present invention has an ultrasound module provided with an ultrasound probe and detachably coupled to the front end of a scope; an ultrasound image diagnosis device electrically connected to the ultrasound probe to process an ultrasound diagnosis image; an endoscopic image diagnosis device electrically connected to the scope to process an endoscopic diagnosis image; and a (Continued)

display for displaying the ultrasonic diagnosis image of the ultrasonic image diagnosis device and the endoscopic diagnosis image of the endoscopic image diagnosis device, and thus the present invention can attachably/detachably use the ultrasound probe at the front end of a conventional endoscope device, so as to reduce the socioeconomic cost of transferring patients to secondary and tertiary hospitals if purchased and used by primary medical personnel who could not purchase expensive conventional equipment.

9 Claims, 6 Drawing Sheets

(58) Field of Classification Search
CPC ..... A61B 8/4411; A61B 8/4416; A61B 1/015; A61B 1/06; A61B 8/4422; A61B 8/445
See application file for complete search history.

(56) References Cited

U.S. PATENT DOCUMENTS

| | | | |
|---|---|---|---|
| 2008/0205715 A1* | 8/2008 | Halmann | A61B 8/467 382/128 |
| 2009/0163767 A1* | 6/2009 | Tsutaki | A61B 8/12 600/104 |
| 2011/0166455 A1 | 7/2011 | Cully et al. | |
| 2017/0143299 A1* | 5/2017 | Kashiwazaki | A61B 1/00094 |
| 2018/0098688 A1* | 4/2018 | Ogawa | A61B 8/445 |
| 2020/0107708 A1 | 4/2020 | Amano | |

FOREIGN PATENT DOCUMENTS

| | | | | |
|---|---|---|---|---|
| WO | 2019200324 A1 | 10/2019 | | |
| WO | WO-2021171608 A1 * | 9/2021 | | A61B 1/018 |

* cited by examiner

ENDOSCOPIC IMAGE DIAGNOSIS DEVICE HAVING DISPOSABLE ULTRASOUND PROBE

CROSS-REFERENCE TO RELATED APPLICATIONS

This application is a U.S. National Stage application of PCT/KR2021/008928 filed 13 Jul. 2021, which claims priority to Korean Patent Application No. 10-2020-0086154 filed 13 Jul. 2020, and Korean Patent Application No. 10-2020-0086155 filed 13 Jul. 2020, the entire disclosures of which are hereby incorporated by reference in their entireties.

TECHNICAL FIELD

The present invention relates to an endoscopic image diagnosis device, in detail, an endoscopic image diagnosis device having a disposable ultrasound probe, the endoscopic image diagnosis device being able to prevent contagion and perform ultrasound diagnosis without using existing high-price ultrasound endoscopic equipment by having a disposable ultrasound probe at a front end of the endoscopic image diagnosis device.

BACKGROUND ART

An endoscope is a medical instrument that can directly observe the inside of the organs or the coelom and is an instrument designed to observe organs, of which diseased parts fundamentally cannot be seen without a surgery or an autopsy, by inserting a device to the organs.

Figure 1:
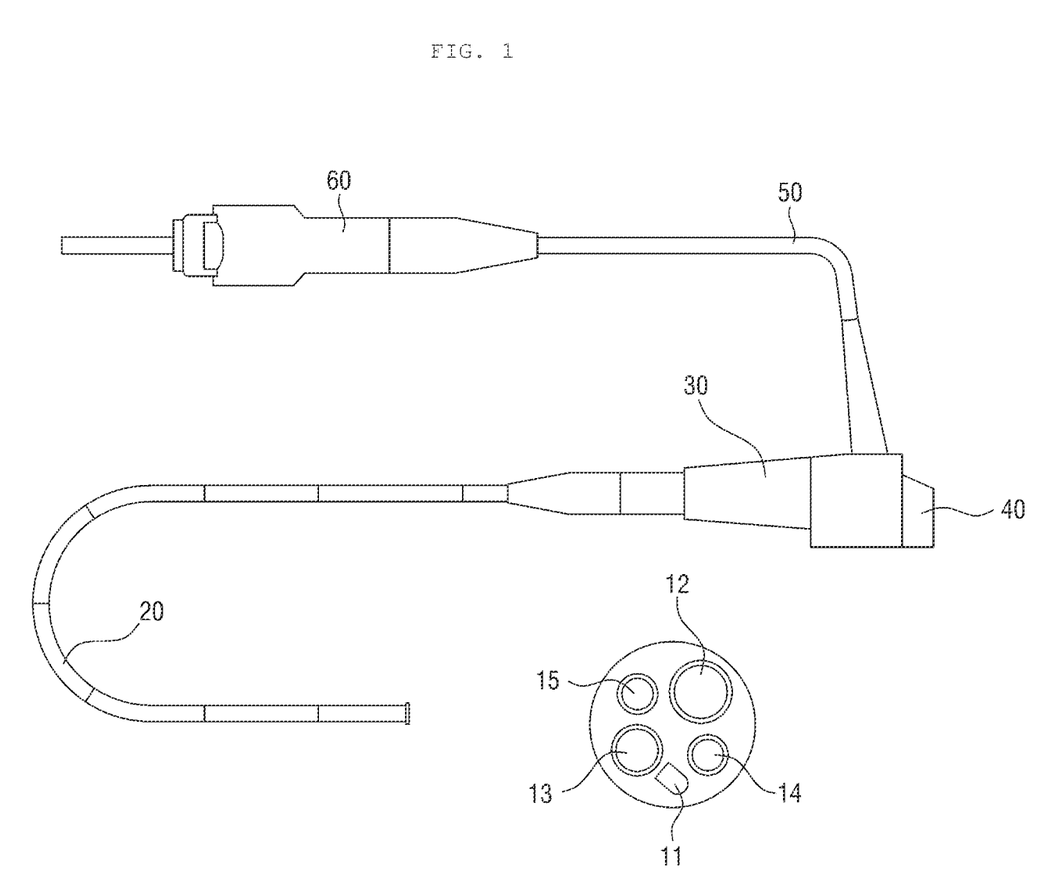
FIG. 1 is a view showing common endoscope equipment of the related art.

Such an endoscope of the related art is shown in FIG. 1.

In general, an endoscope includes an objective lens 13 that captures and transmits an organ image at a scope front end part and a disposal tool that is used to take and dispose of tissues and collect wastes, is composed of a disposal channel 12 that suctions mucus, a nozzle 11 that discharges water or air, and one or more light sources 14 and 15, and is configured to observe organs through the front end of an endoscopic scope 20 by operating an operation unit 30.

The channel 12 is also called a working channel or a biopsy channel, and a biopsy forceps are moved through the channel 12. Suction of air or water when a suction button of the operation unit is pressed is achieved through the working channel.

Light guide lenses 14 and 15 are disposed at both sides of the objective lens 13, and the reason of providing two light guide lenses is for observing without a shadow.

The nozzle is called an air/water nozzle, and air flows into the nozzle. It is also a function of the nozzle to wash out foreign substances from the objective lens by sprinkling water to the objective lens.

Further, a common switch 40 is provided at the operation unit 30, and the operation unit 30 is connected to a connector 60 through a universal code 50 and used.

Common endoscopy using such a device has a problem that although it can observe the mucosa (the outermost part) of the digestive tract, it cannot observe diseased parts of layers (the submucosa or the muscularis mucosa) under or outside the mucosa of the digestive tract.

In order to solve this problem, an examination is also performed using an ultrasound endoscope, if necessary.

That is, unlike visual observation using common endoscopes, by observing a diseased part using ultrasonic waves, it is possible to more accurately perform differential diagnosis of a submucosal tumor, determine the stages of a cancer of the esophagus and a gastric cancer, perform differential diagnosis of a cystic gallstone, a polyp, and a gallbladder cancer, and perform differential diagnosis of a bile duct gallstone, a tumor, a bile duct cancer, and pancreatic diseases.

In other words, an ultrasound diagnosis system has an advantage of being able to obtain images in real time and almost not harming human beings. However, when only a ultrasound diagnosis device is used, it is difficult to obtain images of all diseased parts of a patient, it is possible to obtain only a portion of a diseased part rather than the entire diseased part, and it is not possible to obtain images of a diseased part and the surrounding region, so it is difficult to effectively find a path that reaches a diseased part. Accordingly, it is attempted to obtain accurate diagnosis by simultaneously using an endoscopic image diagnosis device and an ultrasound diagnosis device.

However, ultrasound endoscopic device and equipment is very expensive, so medical centers of a general hospital level or higher have ultrasound endoscope, making accessibility to medicine low. Further, even though ultrasound endoscopes are sterilized and reused, antibiotic resistant bacteria has been recently found on a sterilized endoscope, so a problem that safety of patient may be threatened is being exposed.

SUMMARY OF INVENTION

Technical Problem

In order to solve these problems, an objective of the present invention is to provide an endoscopic image diagnosis device having a disposable ultrasound probe that can be coupled to a common endoscope to use the endoscope as an ultrasound endoscope.

Further, another objective of the present invention is to provide an endoscopic image diagnosis device having a disposable ultrasound probe that can be detachably coupled to the front end of an existing endoscope to be disposable in use.

Further, another objective of the present invention is to provide an endoscopic image diagnosis device having a disposable ultrasound probe in which the direction of ultrasonic waves is the same as the forward movement direction of an endoscope.

Solution to Problem

It is possible to achieve an endoscopic image diagnosis device having a disposable ultrasound endoscope according to an embodiment of the present invention for achieving the objectives by including: an endoscopic probe that is a long tube and has a plurality of holes connecting rear end part to front end part therein; an ultrasound module that has an ultrasound probe emitting ultrasonic waves, which can diagnose the body of a patient, and is detachably coupled to the outer surface of a front end part of the endoscopic scope; an ultrasound image diagnosis device that is electrically connected with the ultrasound probe and processes ultrasound diagnosis images; an endoscopic image diagnosis device that is electrically connected with the endoscopic probe and processes endoscope diagnosis images; and a display that displays ultrasound diagnosis images of the ultrasound image diagnosis device and endoscopic diagnosis images of the endoscopic image diagnosis device.

An endoscopic image diagnosis device according to another embodiment of the present invention for achieving the objectives includes: a scope that is a long tube and has a plurality of holes connecting rear end part to front end part therein; an ultrasound probe that is disposed inside a front end part of the scope and generates and receives ultrasonic waves that can diagnose the body of a patient; an ultrasound image diagnosis device that is electrically connected with the ultrasound probe and processes ultrasound diagnosis images; an endoscopic image diagnosis device that is electrically connected with the probe and processes endoscope diagnosis images; and a display that displays ultrasound diagnosis images of the ultrasound image diagnosis device and endoscope diagnosis images of the endoscopic image diagnosis device.

Advantageous Effects of Invention

Therefore, according to the endoscopic image diagnosis device having a disposable ultrasound probe of the present invention, since the ultrasound probe can be detachably coupled to the front end of a conventional endoscope device in use, there is an effect of reducing the socioeconomic cost of transferring patients to secondary and tertiary hospitals if primary medical personnel, who could not purchase expensive conventional equipment, can purchase and use the device.

Further, according to the endoscopic image diagnosis device having an ultrasound probe of the present invention, since the ultrasound probe can be detachably coupled to the front end of an existing endoscope device in use as a disposable type, there is an effect that it is possible to protect a patient from infection.

Further, according to the endoscopic image diagnosis device having an ultrasound probe of the present invention, since the direction of ultrasonic waves is the same as the forward movement direction of the endoscope, there is an effect that it is possible to easily diagnose a diseased part.

Further, according to the endoscopic image diagnosis device having an ultrasound probe of the present invention, since the ultrasound probe can be detachably coupled to the front end of existing endoscope equipment in use, conventional high-price ultrasound endoscope equipment is not required.

DESCRIPTION OF EMBODIMENTS

The terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept of the term to describe most appropriately the best method he or she knows for carrying out the invention.

Throughout the present specification, unless explicitly described otherwise, "comprising" any components will be understood to imply the inclusion of other components rather than the exclusion of any other components. Further, the terms "part", "unit", "module", "apparatus" and the like mean a unit for processing at least one function or operation and may be implemented by a combination of hardware and/or software.

It should be understood throughout the specification that the term "and/or" includes any and all combinations of one or more of the associated items. For example, the meaning of "a first item, a second item and/or a third item" not only means a first, second, and third item, but also any and all combinations that can be presented from two or more items of the first and second and third items.

In each step, reference characters (e.g., a, b, c, . . . ) are used for convenience without limiting the order of each step, and each step may occur different from the orders described herein unless specific orders are clearly described in contexts. That is, each step may occur in the order described herein, may be substantially simultaneously performed, or may be performed in a reverse order.

Hereinafter, an embodiment of the present disclosure will be described with reference to the accompanying drawings.

Figure 2:
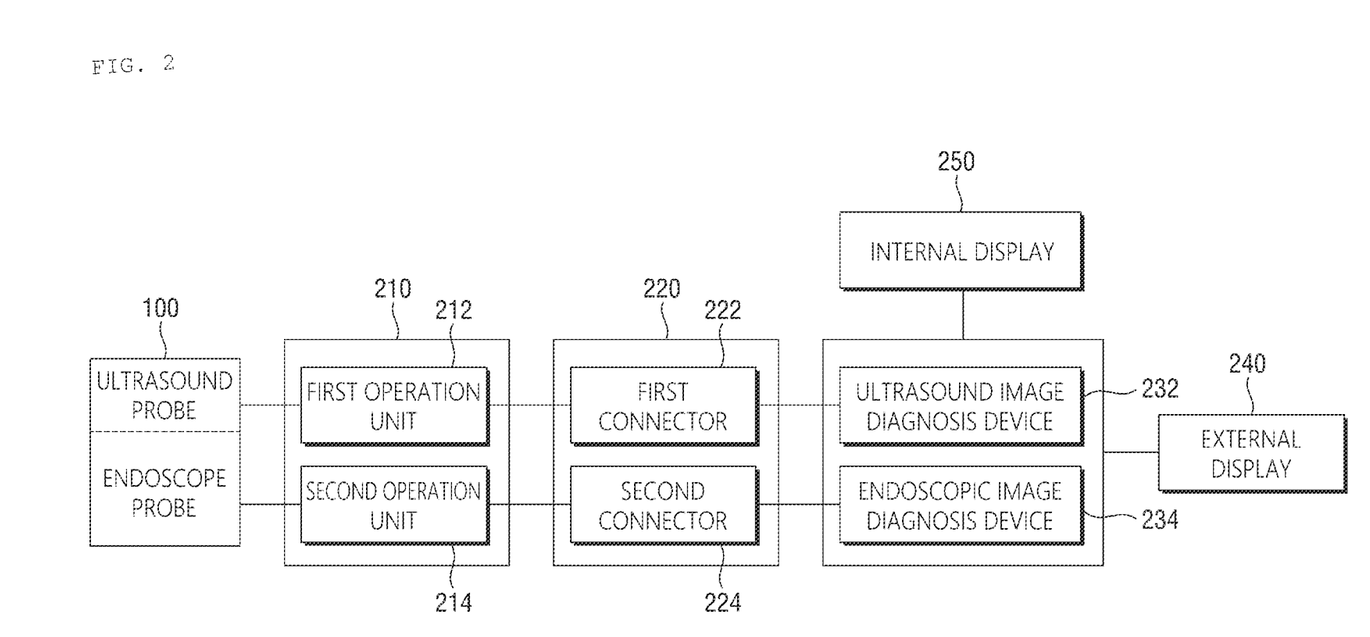
FIG. 2 is a view showing the main configuration of an endoscopic image diagnosis device having a disposable ultrasound probe according to an embodiment of the present invention.

FIG. 2 is a view showing the main configuration of an endoscopic image diagnosis device having a disposable ultrasound probe according to an embodiment of the present invention. As shown in the figure, according to an endoscopic image diagnosis device having a disposable ultrasound probe of the present invention, an endoscope front end part 100 composed of an endoscopic scope and an ultrasound module and an operation unit 210 for operating the front end part through a scope 20 electrically connected to the endoscope front end part 100 are connected, images collected through the operation unit 210 are transmitted to a connector 220, the images of the connector 220 are transmitted to image diagnosis devices 232 and 234, and final images are displayed on an internal display 250 and/or an external display 240.

In detail, the endoscope front end part 100 is operated in a form in which a common endoscopic scope and an ultrasound module is combined, the endoscopic scope is operated by a second operation unit 214, and probe 140 of the ultrasound module is operated by a first operation unit 212.

The operation unit 210 is generally designed to be operable by a left hand, so it is possible to freely operate a suction and air discharge port with left index finger and middle finger while operating a direction handle with a left thumb. Up, down, left, and right handles each have a lock. Further, various switches for taking and storing pictures may be provided.

Endoscopic images by operation of the second operation unit 214 are transmitted to the endoscopic image diagnosis device 234 through a second connector 224 and used as diagnosis image, and ultrasound images by operation of the first operation unit 212 are transmitted to the ultrasound image diagnosis device 232 through a first connector 222 and used as diagnosis images.

The endoscopic image diagnosis device 234 is electrically connected to the endoscopic scope and operated to process endoscope diagnosis images, and the ultrasound image diagnosis device 232 is electrically connected with the ultrasound probe and operated to process ultrasound diagnosis images.

Further, the ultrasound diagnosis images of the ultrasound image diagnosis device 232 and the endoscope diagnosis images of the endoscopic image diagnosis device 234 are displayed on the internal display 250 and/or the external display 240.

The internal display 250 and/or the external display 240 are configured to display the operation states and images of endoscopic images and ultrasound images.

The present invention is characterized by an endoscopic image diagnosis device having a disposable ultrasound probe, the endoscopic image diagnosis device being able to prevent infection and perform ultrasound diagnosis without using existing high-price ultrasonic endoscopic equipment.

To this end, the present invention is configured such that an ultrasound probe can be detachably attached to the front end of an existing endoscopic probe in use.

Figure 3:
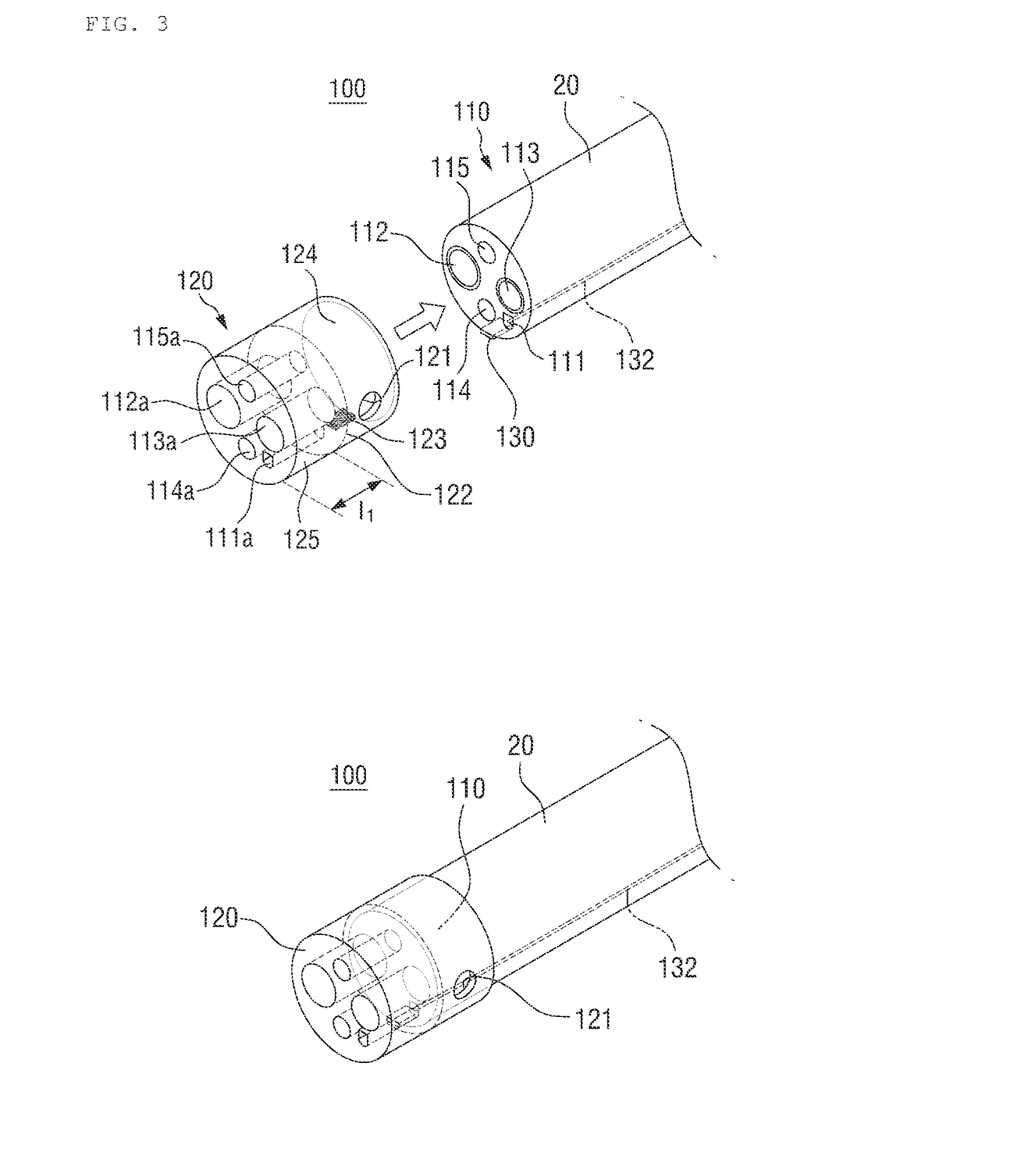
FIG. 3 is a view showing an ultrasound module according to an embodiment of the present invention.

Referring to FIG. 3 showing an ultrasound module according to an embodiment of the present invention, an ultrasound module 120 is detachably coupled to a scope front end part 110.

That is, the present invention consists of an endoscopic scope that is a long tube and has a plurality of holes connecting rear end part to the scope front end part 110 and an ultrasound module 120 that has an ultrasound probe emitting ultrasonic waves, which can diagnose the body of a patient, and is detachably coupled to the outer surface of the scope front end part 110.

Further, connectors 123 and 130 are provided so that images of the ultrasound probe can be easily transmitted to the ultrasound image diagnosis device 232 by such attachment/detachment, and an ultrasonic wave signal cable 132 may be bonded to the outer surface of an existing probe 20 in use so that a signal of the connector 130 can be transmitted to the ultrasound image diagnosis device 232.

The ultrasound module 120 is configured in a front end cap shape and the material thereof is an elastic material such as silicon and plastic. The probe protrudes about 3 to 4 mm from a mounting line so that the ultrasound probe is stably supported in the module and the visual field of the endoscope can be secured.

That is, when the ultrasound module 120 with a protruding front end part of the present invention is mounted at the front end of a scope, a gap is defined between the endoscope front end having a camera attached thereto and a mucosa of a patient. Accordingly, even if the end of an endoscope comes in contact with a mucosa, the lens of the endoscope is positioned at 3 to 4 mm behind, so a visual field can be secured.

The fact that a gap is defined between the endoscopic scope and a mucosa due to the front end part of the ultrasound module means that a visual field that would not be seen due to contact with the mucosa if the ultrasound module is not mounted is secured. Accordingly, it may be another advantage that it is possible to see the next direction to go.

Further, the present invention is characterized in that the ultrasound probe can be detachably attached to existing endoscope devices in use.

To this end, referring to the lower one in FIG. 3, when the ultrasound module 120 is coupled to the scope front end part 110 of the scope 20, the connectors 123 and 130 are connected and electrical connection is possible through the ultrasonic wave signal cable 132.

That is, when a first connection port 123 electrically connected to the ultrasound probe is coupled to the outer surface of the front end part of the endoscopic probe, the second connection port 130 at the front end part of the endoscopic scope is positioned to face the first connection port and the front end part of the endoscopic scope is inserted in close contact to a mounting line, whereby coupling is finished.

The front end of the scope 20, that is, the endoscopic scope includes an objective lens 113 that captures and transmits organ images, a disposal channel 112 that has a disposal tool, which is used to take or dispose of tissues and collect wastes, and suctions mucus, a nozzle 111 for discharging water or air, and one or more light sources 114 and 115, and is configured to perform general endoscope functions.

Accordingly, through-holes through which respective devices can be moved in and out are formed in the ultrasound module 120 that is detachably coupled to the front end part of the scope 20 so that the objective lens 113, the nozzle 111, the channel 112, and the one or more light sources 114 and 115 of the endoscopic scope can be operated.

That is, even though the ultrasound module 120 is coupled to the scope front end part 110, existing endoscope devices can perform their functions through the through-holes.

Referring to FIG. 3, it can be seen that through-holes through which respective devices can be moved in and out are formed in the ultrasound module 120. That is, it can be seen that a channel through-hole 112a is formed on a facing surface of the channel 112, and light guide through-holes 114a and 115a, objective lens through-hole 113a, and a nozzle through-hole 111a are formed on facing surfaces of the light guide 114 and 115, the objective lens 113, and the nozzle 111, respectively.

The ultrasound module 120 is composed of a probing section 125 having the through-holes and an ultrasound probe, and a coupling section 124 coupled to the scope front end part 110.

It can be seen from the figure that the probing section 125 has a thickness L1 from the front end part.

Further, a mounting line 112 is protruded at a side on the inner surface of the ultrasound module 120 and a side hole 121 is formed at a side of the mounting line so that the ultrasound module 120 and the scope front end part 110 can be accurately coupled. Accordingly, when the ultrasound module 120 is fitted on the front end part of the scope, the objective lens 113 of the endoscopic scope can be positioned to face the side hole 121 and then the scope front end part 110 is inserted in close contact into the coupling section 124 to the mounting line 122.

The scope front end part 110 inserted in close contact to the mounting line 122 is forcibly coupled by the coupling section 124.

Further, in order to be able to effectively take and observe endoscopic images and ultrasound images and simply fit a cap for use without mechanically changing existing endoscope devices, an ultrasound probe is configured at positions corresponding to the nozzle 111, the channel 112, the objective lens 113, and the one or more light probes 114 and 115, whereby it is possible to simultaneously obtain ultrasound and endoscopic images.

Further, due to the ultrasound module and the connection ports, it is possible to prevent infection by removing an ultrasound module used once and using another ultrasound module as a disposable item.

Hereafter, various embodiments that can configure an ultrasound probe are described with reference to the drawings.

Figure 4:
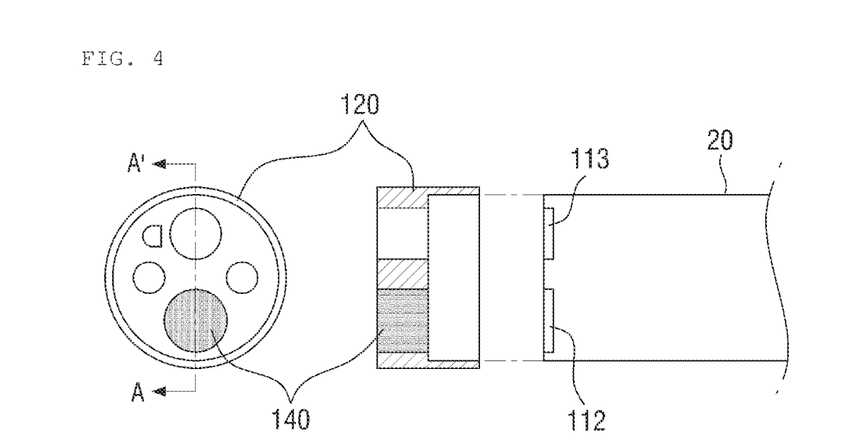
FIG. 4 is a view exemplifying an ultrasound module having an ultrasound probe according to a first embodiment.

Referring to FIG. 4 that is a view showing an ultrasound module having an ultrasound probe according to a first embodiment, the size of an ultrasound probe 140 formed in the ultrasound module 120 corresponds to the channel 112 and the ultrasound probe 140 is positioned on the facing surface of the channel 112 when the ultrasound module 120 is coupled to the front end part of the scope.

That is, the ultrasound probe 140 formed in the probing section 125 is formed at a position facing the channel 112 of the endoscopic scope formed at the front end of the scope 20, so the ultrasound probe 140 is coupled to cover the channel 112 in use.

The channel has a disposal tool used to take and dispose of tissue and collect wastes and operates to suction and dispose of mucus, so it is not used much in a diagnosis step that uses endoscopic images and ultrasound images. Therefore, the ultrasound probe 140 is positioned to cover the channel 112 so that endoscopic images and ultrasound images can be simultaneously obtained.

Of course, when a diagnosis finished, it is possible to separate the ultrasound module 120 and take or dispose of tissues using the channel 112.

Referring to FIG. 4, it can be seen that the ultrasound probe 140 fixed by the ultrasound module 120 is positioned on the facing surface of the channel 112 of the endoscopic scope.

Accordingly, other devices formed in the endoscopic scope other than the channel can perform fundamental functions through the through-holes, respectively.

Figure 5:
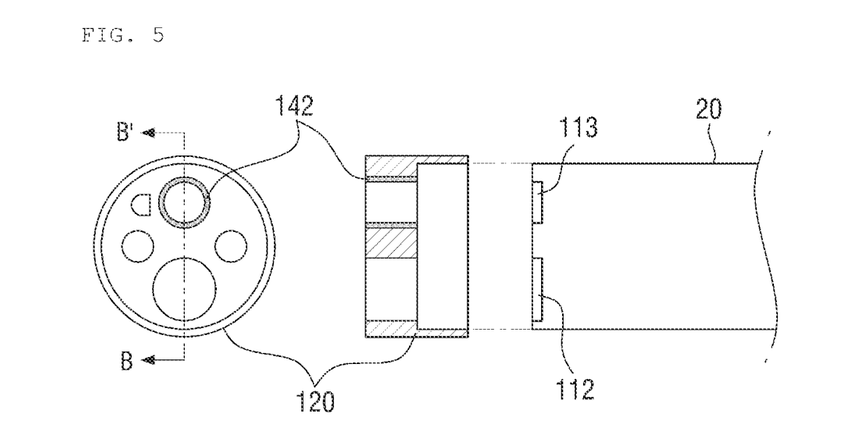
FIG. 5 is a view exemplifying an ultrasound module having an ultrasound probe according to a second embodiment.

Referring to the figure exemplifying an ultrasound module having an ultrasound probe according to a second embodiment of FIG. 5, an ultrasound probe 142 is configured in a ring shape having size surrounding the outer surface of an objective lens 113, so when the an ultrasound probe 142 is coupled to the front end part of a scope, the ultrasound probe 142 surrounds the outer surface of the objective lens 113.

That is, the ultrasound probe 142 according to the second embodiment is formed in the probing section 125 at a position facing the objective lens 113 of the endoscopic scope 20, so when the ultrasound probe 142 is coupled, the ultrasound probe 142 having a ring shape surrounds the outer surface of the objective lens 113.

This has an advantage that all existing endoscope devices can be used.

That is, in order to couple the ultrasound probe to the outer surface of the scope, the objective lens of the endoscopic scope is positioned to face the side hole and then the front end of the scope is inserted in close contact to the mounting line, so the ultrasound probe 142 is coupled to surround the objective lens 113, and the nozzle 111, the channel 112, the objective lens 113, and the one or more light probes 114 and 115 configured in the endoscopic scope can be moved in and out through the through-holes, respectively, to perform their functions.

Figure 6:
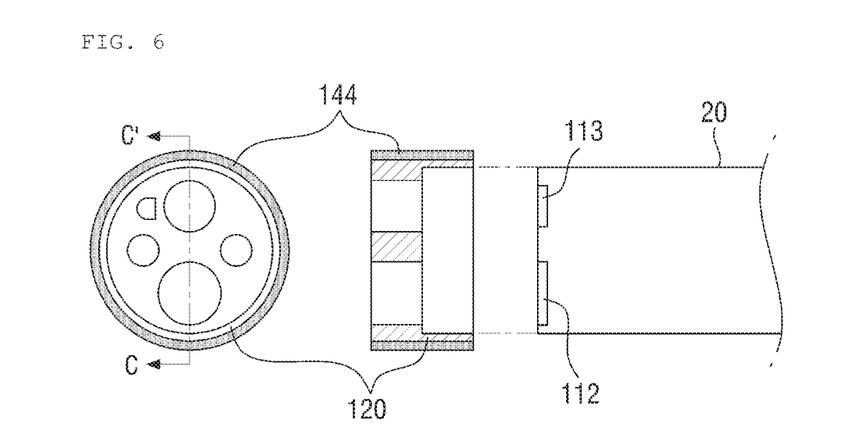
FIG. 6 is a view exemplifying an ultrasound module having an ultrasound probe according to a third embodiment.

Referring to the figure exemplifying an ultrasound module having an ultrasound probe according to a third embodiment of FIG. 6, an ultrasound probe 144 may be configured and used in a ring shape on the outer surface of the front end part of the ultrasound module 20.

Referring to the figure, since the ultrasound probe 144 is configured in a ring shape on the outer surface of the front end part of the ultrasound module 20, there is an advantage that existing endoscope devices can be used in the same way while performing an ultrasound function.

The present invention can be configured such that it is possible to prevent infection and perform ultrasound diagnosis without using existing high-price ultrasound endoscope equipment by providing an ultrasound probe at the front end part of an endoscopic image diagnosis device.

It is apparent that such an ultrasound probe may be detachably coupled to be used as a disposable product and to prevent infection.

To this end, the present invention is configured such that an ultrasound probe can be detachably coupled to the front end of an existing endoscopic probe to be used.

Figure 7:
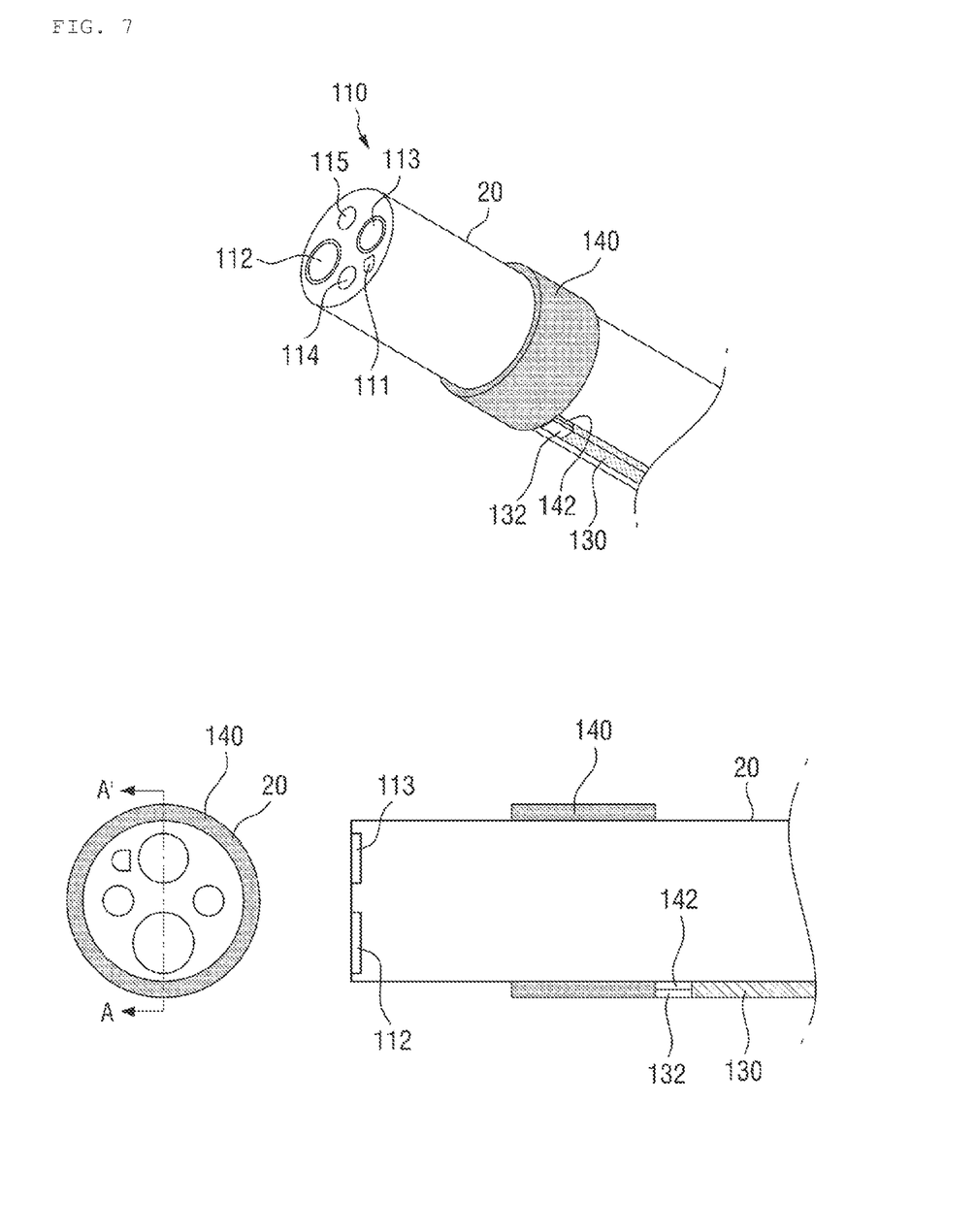
FIG. 7 is a view showing in detail the configuration of an endoscope front end part according to an embodiment of the present invention.

Referring to FIG. 7 that is a detailed configuration view of an endoscope front end part according to an embodiment of the present invention, the scope 20 is a long tube and has a plurality of holes connecting rear end part to the front end part 110 formed therein.

Further, an objective lens 113 that captures and transmits organ images of a body and a disposal channel 112 that is provided with a disposal tool used to take and dispose of tissues and collect wastes and for suctioning mucus are provided in the front end of the scope 20, that is, the endoscopic scope.

Further, a nozzle 111 for discharging water or air and one or more light sources 114 and 115 may be included.

The present invention is characterized in that an ultrasound probe that can be simply detachably coupled to an existing endoscopic probe having the configuration described above in use enables to simply perform diagnosis using ultrasonic waves using existing endoscope equipment even without additional specific equipment.

Further, the present invention is characterized in that an ultrasound probe is coupled to be able to perform all of endoscope examination and disposal using an existing endoscopic scope without being affected by an additional ultrasound probe.

To this end, according to an endoscopic image diagnosis device having a detachable radial emissive ultrasound endoscope of the present invention, a hollow ring-shaped ultrasound probe 140 that is coupled to surround the outer surface of a scope can be detachably coupled in the scope front end part 110.

Of course, as described above, it is apparent that the ultrasound probe 140 may be used in a fixed type rather than a detachable type.

The ultrasound probe 140 having this configuration has an effect that it can easily diagnose diseased parts because the direction of ultrasonic waves is the same as the forward movement direction of the endoscope.

Referring to figures, the ultrasound probe 140 is detachably coupled in a band form in the scope front end part 110, so there is an advantage that existing endoscope devices can be used in the same way while performing an ultrasound function It is exemplified in this embodiment that the ultrasound probe is detachably coupled in a band form in the scope front end part of the scope, but the present invention is not limited thereto and it is apparent that the ultrasound probe may be configured to be detachably coupled at any necessary position from the front end of the scope.

The ultrasound probe 140 operates to generate, receive, and transmit ultrasonic waves, which can diagnose the body of a patient, to the ultrasound image diagnosis device 232.

Further, the ultrasound probe 140 may have a first connector 142 for signal transmission at a side of the ultrasound probe 140 so that diagnosis images can be easily transmitted to the ultrasound image diagnosis device 232, and may have a second connector 130a connected to the first connector 142 at a side of the existing probe 20 so that signals from the connector 130a can be transmitted to the ultrasound image diagnosis device 232.

A signal transmitted to the second connector 130a is transmitted to the ultrasound image diagnosis device 232 through the ultrasonic wave signal cable 130a coupled or bonded to the outer surface of the existing scope 20.

Referring to the upper one in FIG. 7, it can be seen that the ultrasound probe 140 is disposed in the scope front end part 110, and the connectors 130a and 142 and the ultrasonic wave signal cable 130aa are electrically connected.

Referring to the lower one in FIG. 7, which shows a cross-sectional shape seen in the direction of an arrow at the front end part of the scope in the upper one in FIG. 3, it can be seen that the ultrasound probe 140 is coupled in a band form to the outer surface of the scope 20.

It is exemplified in figures that the ultrasound probe 140 is formed inside at a distance "L1" from the front end of the scope 20, that is, the endoscopic scope, but, as described above, the ultrasound probe 140 of the present invention may be formed at any position, that is, at any position inside "L1" from the front end of the endoscopic scope.

Further, the endoscopic image diagnosis device having a detachable radial emissive ultrasound endoscope of the present invention may further have a front end cap to be able to secure the visual field of the endoscope.

Figure 8:
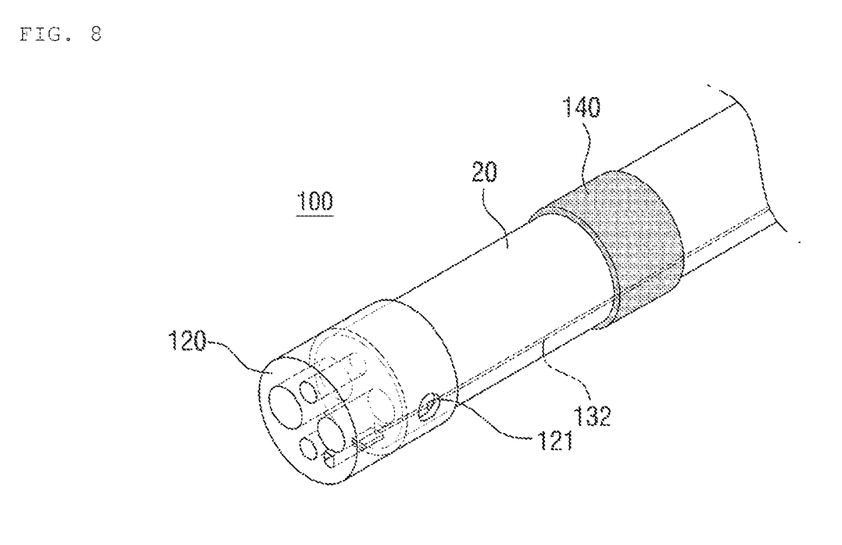
FIG. 8 is a view showing the configuration of an endoscope front end part according to another embodiment of the present invention.

Referring to FIG. 8 that is a detailed configuration view of an endoscope front end part according to another embodiment of the present invention, a front end cap is configured at the front end of the scope of the present invention.

The front end cap 120 is made of silicon or plastic that is an elastic material, and the front end part thereof protrudes about 3 to 4 mm from the mounting line to be able to secure the visual field of the endoscope.

That is, when the front end cap with the protruding front end part of the present invention is mounted at the front end of a scope, a gap is defined between the endoscope front end having a camera attached thereto and a mucosa of a patient. Accordingly, even if the end of an endoscope comes in contact with a mucosa, the lens of the endoscope is positioned at 3 to 4 mm behind, so a visual field can be secured.

The fact that the front end cap and a mucosa are spaced apart means that a visual field that would not be seen due to contact with the mucosa if the front end cap is not mounted is secured. Accordingly, it may be another advantage that it is possible to see the next direction that the front end goes.

Referring to FIG. 8, it can be seen that through-holes through which respective devices can be moved in and out are formed in the front end cap 120. That is, it can be seen that a channel through-hole 112a is formed on a facing surface of the channel 112, and light guide through-holes, an objective lens through-hole, light guide through-hole, and a nozzle through-hole are formed on facing surfaces of the light guide 114 and 115, the objective lens 113, and the nozzle 111, respectively.

Further, a mounting line protrudes from a side on the inner surface of the ultrasound front end cap 120 so that the front end cap 120 and the front end part 110 of the scope can be accurately coupled, and a side hole 121 is formed through a side of the mounting line. Accordingly, when the front end cap is fitted on the front end of the endoscopic probe, the objective lens 113 of the endoscopic scope can be positioned to face the side hole 121 and then the front end of the scope is inserted in close contact into the coupling section 124 to the mounting line in use.

Although the present invention was described with reference to the detailed embodiments, it is apparent to those skilled in the art that the present invention may be changed and modified in various ways within the scope of the present invention, and it should be noted that the changes and modifications are included in claims.

The invention claimed is:

1. An endoscopic image diagnosis device having a disposable ultrasound endoscope, the endoscopic image diagnosis device comprising:
   a scope that is a long tube and has a plurality of holes connecting rear end part to front end part therein;
   an ultrasound module that has an ultrasound probe emitting ultrasonic waves, which can diagnose the body of a patient, and is detachably coupled to the outer surface of a front end part of the scope;
   an ultrasound image diagnosis device that is electrically connected with the ultrasound probe and processes ultrasound diagnosis images;
   an endoscopic image diagnosis device that is electrically connected with the endoscopic probe and processes endoscope diagnosis images; and
   a display that displays ultrasound diagnosis images of the ultrasound image diagnosis device and endoscope diagnosis images of the endoscopic image diagnosis device,
   wherein an endoscopic scope including an objective lens that captures and transmits organ images, a disposal channel which is used to take or dispose of tissues and collect wastes, and suctions mucus, a nozzle that discharges water or air, and one or more light sources is provided at a front end of the scope; and
   wherein the ultrasound module has the ultrasound probe having a size that is the size of the disposal channel, and is configured such that when the ultrasound module is coupled to a scope front end part, the ultrasound probe is positioned on a facing surface of the disposal channel.

2. The endoscopic image diagnosis device of claim 1, wherein the ultrasound module is composed of a probing section in which the ultrasound probe is disposed and a coupling section coupling the probing section to the scope front end part, and
   through-holes through which the objective lens, the nozzle, and one or more light probes can be moved in and out are formed in the probing section of the ultrasound module.

3. The endoscopic image diagnosis device of claim 1, wherein the ultrasound module has a side hole, so when the ultrasound module is coupled to the scope front end part, the objective lens of the scope is positioned to face the side hole and then the front end part of the scope is inserted in the side hole.

4. The endoscopic image diagnosis device of claim 1, wherein the ultrasound module has a first connection port electrically connected with the ultrasound probe, and wherein the ultrasound module is fitted on the outer surface of a front end part of the scope such that a second connection port disposed at the front end part of the scope and the first connection art are connected.

5. The endoscopic image diagnosis device of claim 1, wherein an endoscopic scope including an objective lens that captures and transmits organ images, a disposal channel, which is used to take or dispose of tissues and collect wastes, and suctions mucus, a nozzle that discharges water or air, and one or more light sources is provided at a front end of the scope, and wherein the ultrasound probe is configured in a ring shape having a size surrounding the outer surface of the objective lens, and is coupled to a scope front end to surround the outer surface of the objective lens.

6. The endoscopic image diagnosis device of claim 1, wherein the ultrasound probe is configured in a ring shape on the outer surface of a front end part of the ultrasound module.

7. The endoscopic image diagnosis device of claim 6, wherein an endoscopic scope including an objective lens that captures and transmits organ images, a disposal channel, which is used to take or dispose of tissues and collect wastes, and suctions mucus, a nozzle that discharges water or air, and one or more light sources is provided at a front end of the scope, and wherein the ultrasound module is composed of a probing section in which the ultrasound probe is disposed and a coupling section coupling the probing section to a scope front end part, and through-holes through which the objective lens, the channel, the nozzle, and the one or more light sources can be moved in and out are formed in the probing section of the ultrasound module.

8. The endoscopic image diagnosis device of claim 6, wherein the ultrasound module has a side hole, so when the ultrasound module is coupled to the scope front end part, the objective lens of the scope is positioned to face the side hole and then the front end part of the scope is inserted in the side hole.

9. The endoscopic image diagnosis device of claim 6, wherein the ultrasound module has a first connection port electrically connected with the ultrasound probe, and wherein the ultrasound module is fitted on the outer surface of a front end part of the scope such that a second connection port disposed at the front end art of the scope and the first connection part are connected.

* * * * *